United States Patent [19]

Mente

[11] Patent Number: 4,851,217

[45] Date of Patent: Jul. 25, 1989

[54] ALL AQUEOUS FORMULATIONS OF ORGANO-PHOSPHOROUS PESTICIDES

[75] Inventor: Donald C. Mente, Grosse Ile, Mich.

[73] Assignee: BASF Corporation, Parsippany, N.J.

[21] Appl. No.: 47,035

[22] Filed: May 5, 1987

[51] Int. Cl.$^4$ .................. A61K 31/45; A01N 57/00
[52] U.S. Cl. ............................... 424/83; 514/80;
514/108; 514/122; 514/134; 514/937; 514/938;
514/941
[58] Field of Search .............. 514/53, 80, 86, 94,
514/103, 119, 122, 128, 127, 130, 132, 135, 136,
144, 147, 187, 191, 249, 351, 354, 355, 388, 398,
417, 460, 461, 467, 477, 478, 481, 471, 521, 531,
576, 598, 641, 751, 781, 788, 937, 940, 941, 963,
970, 971, 974, 975; 324/78, 419; 71/3, 27, 35,
70, 83, 88, 93, 95, 98, 100, 103, 118; 560/240,
198; 564/505

[56] References Cited

U.S. PATENT DOCUMENTS

| | | | |
|---|---|---|---|
| 3,258,326 | 6/1966 | Rabussier | 514/970 |
| 3,894,149 | 7/1975 | Mast | 514/941 |
| 4,075,332 | 2/1978 | Oswald et al. | 514/127 |
| 4,107,302 | 8/1978 | Watanabe | 514/86 |
| 4,195,083 | 3/1980 | Hoy et al. | 514/132 |
| 4,310,520 | 1/1982 | Narazaki | 514/89 |
| 4,324,781 | 4/1982 | Okamoto et al. | 424/78 |
| 4,396,417 | 8/1983 | Lissant | 514/504 |
| 4,450,001 | 5/1984 | Kaneko et al. | 71/118 |
| 4,464,193 | 8/1984 | Kaneko et al. | 71/83 |

Primary Examiner—Douglas W. Robinson
Assistant Examiner—Raymond J. Henley, III
Attorney, Agent, or Firm—Bill C. Panagos

[57] ABSTRACT

A composition of matter and method of making the composition which relates to an all aqueous, phase stable emulsion of organophosphorous pesticides which is free of organic solvents. The composition comprises from about 40 to 95 percent by weight of an organophosphorous selected from the group consisting of phosphates, phosphorothioates and phosphorothionates, and mixtures thereof, from about 3 to 10 percent by weight of an nonionic block, heteric, heteric/block copolymer of ethylene oxide and propylene oxide, from about 3 to 16 percent by weight urea, and about 20 to 50 percent water. The composition is made by blending these components together under moderate agitation.

4 Claims, No Drawings

ALL AQUEOUS FORMULATIONS OF ORGANO-PHOSPHOROUS PESTICIDES

BACKGROUND OF THE INVENTION

1. Field of the Invention

The present invention relates to phase stable aqueous formulations of organo-phosphorous pesticides, and particularly phosphorothioate pesticides, which contain no organic solvents.

This invention further relates to a method for producing all aqueous formulations of organo-phosphorous pesticides, and particularly phosphorothioate pesticides, which reduce the malodor problems associated with organophosphorous pesticides, and particularly phosphorothioate pesticides.

2. Description of the Material Art

Hoy et al, U.S. Pat. No. 4,195,083, disclose a self-emulsifiable liquid pesticide concentrate which contains from about 65 to 95 percent by weight of a liquid pesticide compound or a liquid mixture of a liquid pesticide and a solid pesticide compound. Phosphorothioates are disclosed as suitable pesticides. The compositions also include an emulsifier and a solvent for the pesticide. The solvent may or may not be present and is used to dissolve the pesticide compound and bring it into the emulsion. A emulsion so formed is termed non-aqueous in that only about 3 percent water is present in the solution. The solution is also termed solvent free. However, the solutions usually contain up to about 10 percent solvent. The pesticide is used as a dip for livestock to control ectoparasites, such as fleas and ticks.

The present invention differs from Hoy et al because the present invention is an all aqueous formulation in contrast to the non-aqueous formulation of Hoy et al. Further, the present invention does not employ any organic solvents, whereas Hoy et al, although disclosed as solvent free, use up to about 10 percent organic solvents. Accordingly, the present invention differs from Hoy et al.

Lissant, U.S. Pat. No. 4,396,417, discloses non-Newtonian agricultural formulations which are thixotropic high internal phase ratio emulsions containing insecticides which are useful in agricultural applications. The thixotropic fluid of Lissant exhibits variable viscosity when the shear rate is varied. When the fluids are pumped slowly at low shear rates, they behave as though they are extremely viscous fluids but as the pumping rate is increased, and the shear rate increases, the fluids appear to shear thin and behave as low viscosity fluids. Lissant discloses oil-in-water and water-in-oil emulsions and emulsions where water-like substances are employed in the place of water.

The present invention is not a non-Newtonian thixotropic gel structure such as Lissant. Further, the present invention utilizes a surprisingly high content of water and no organic solvents to suspend a phosphorothioate type insecticide in an aqueous emulsion. Further, Lissant does not utilize the same nonionic surfactants in the present invention as emulsifiers and urea as a phase stabilizer. Accordingly, the present invention differs from Lissant.

SUMMARY OF THE INVENTION

The present invention is an aqueous, phase stable emulsion of organo-phosphorous pesticides, and particularly phosphorothioate pesticides, and a method for producing the same. The compositions of the present invention are entirely free of organic solvents and are comprised of a surprisingly high level of phosphorothioate, which is present in an amount of about 40 to 95 percent by weight of the composition, urea, present in an amount of about 3 to 16 percent by weight of the composition, a nonionic surfactant present in the amount of about 3 to 10 percent by weight of the composition, and water present in an amount of from about 20 to 50 percent by weight of the composition. The surfactant is non-ionic and selected from block, heteric and heteric/block copolymers of propylene oxide and ethylene oxide. Specifically, the preferred block copolymers of propylene oxide and ethylene oxide are the PLURONIC ® series from BASF Corporation, namely PLURONIC ® P103, P104, and P105. Of these surfactants, PLURONIC ® P103 is preferred. Finally, the urea acts to ameliorate the malodor attendant with use of organo-phosphorous compounds, and particularly phosphorothioate compounds. The urea also acts as a phase stabilizer in the formulation, and in combination with the surfactants, exhibits some thickening properties.

The method for producing the all aqueous organo-phosphorous formulation follows. Typically, the surfactant is added to water under moderate agitation conditions. It is preferred to melt the surfactant when using cold water. A phase stabilizer such as urea is optionally added under moderate agitation and the pesticide is added under continued moderate agitation. Those skilled in the art will recognize that the order of mixing is not critical, except it be done under moderate agitation. Phase separation is prevented by use of the phase stabilizer, and, if any phase separation occurs after extended periods of storage, the formulation can be easily re-mixed by simple agitation. The compositions of the present invention are less toxic to fish and wildlife owing to the absence of organic solvents. Further, organic solvents have a detrimental effect on automobile finishes. The absence of organic solvents makes the formulations of the present invention safe to use around automobiles. Thus, the pesticide compositions of the present invention may be sprayed on trees, shrubs, flowers, and in agricultural and residential settings with less concern for harming the environment and without fear of harming automobile finishes.

DETAILED DESCRIPTION OF THE PREFERRED EMBODIMENT

The present invention is an all aqueous, phase stable formulation for organo-phosphorous pesticides, and particularly for phosphorothioate pesticides, as well as a method for producing the same.

The pesticides for use in the compositions may be any pesticides which are organo-phosphorous pesticides of the phosphate, phosphorothioate, and phosphorothionate types. These include such chemicals as 2-chloro-1(2,4 dichlorophenyl) vinyl diethyl phosphate, O,O,O′-,O′-tetraethyl S,S′-methylenediphosphorodithioate, [2,3-p-dioxanedithiol S,S-bis(O,O-diethyl phosphorodithionate)], O,O-diethyl-O-2-isopropyl-4-methyl-6-pyrimidyl phosphorothionate, O,O-diethyl O-2,4-dichlorophenyl phosphorothionate, O,O-diethyl S-(p-chlorophenylthio) methyl phosphorodithioate, O,O-diethyl O,4-bromo-2,5-dichlorophenyl phosphorothionate, O,O-dimethyl O-1,2-dibromo-2,2-dichloroethyl phosphate, dimethyl 3-methyl-4-methylthiophenyl phosphorothionate, O,O-dimethylphosphorodithioate of diethylmercaptosuccinate, and mixtures thereof.

Solid pesticides may also be included in addition to one or more of the liquid pesticides selected from the group consisting of O,O-diethyl O-3,5,6-trichloro-2-pyridylphosphorothionate, O,O-dimethyl O-(2,4,5-trichlorophenyl) phosphorothionate, N-(mercaptomethyl)-phthalimido S-(O,O-dimethyl phosphorodithioate, 2-chloro-1-(2,4-dichlorophenyl) phosphorothionate, O,O,O',O-tetraethyl S,S'-methylenediphosphorodithioate, O,O-dimethyl O-(3-methyl-4-nitrophenyl) phosphorothionate and mixtures thereof. The solid and liquid pesticides may be used as mixtures with each other. Those skilled in the art will recognize that the given list of organo-phosphorous compounds is not exhaustive but rather is indicative of the compounds which may be utilized in the present invention. Thus, the present invention envisions the use of all organo-phosphorous compounds of the types mentioned for use as the active pesticide agent. The pesticides are present in a pesticidally effective amount, and preferably present in an amount of from about 40 to 95 percent by weight of the composition.

The composition of the present invention also includes a surfactant, present in an amount sufficient to emulsify the compositions, and preferably, present in an amount of from about 3 to 10 percent by weight of the composition. The surfactant is preferably a non-ionic block, heteric or heteric/block copolymer of propylene oxide and ethylene oxide. The polyoxyethylene-polyoxypropylene block copolymer of use in the present invention is a cogeneric mixture of conjugated polyoxyethylene-polyoxypropylene compounds corresponding to the following formula:

$$Y[(C_3H_6O)_n(C_2H_4O)_mH]x_x \qquad (I)$$

wherein Y is the residue of an organic compound having from about 1 to 6 carbon atoms and containing x reactive hydrogen atoms in which x has a value of at least about 1, n has a value such that the molecular weight of the hydrophobe base is about 900 to 12,000 and m has a value such that the oxyethylene chains constitute about 10 to 80 weight percent of the compound. Falling within the scope of the definition for Y are, for example, propylene glycol, glycerine, pentaerythritol, trimethylolpropane, ethylene diamine and mixtures thereof. The oxypropylene chains optionally, but advantageously, contain small amounts of oxyethylene and oxybutylene groups and the oxyethylene chains also optionally, but advantageously, contain small amounts of oxypropylene and oxybutylene groups. These compositions are more particularly described in U.S. Pat. Nos. 2,677,700, 2,674,619 and 2,979,528.

Nonionic surfactants which are particularly applicable are those wherein Y is propylene glycol, and the resulting formula is:

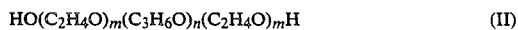

$$HO(C_2H_4O)_m(C_3H_6O)_n(C_2H_4O)_mH \qquad (II)$$

wherein n has a value such that the molecular weight of the hydrophobe is from about 900 to 4000 and m is the same as in formula (I) above. Representative surfactants of this sort are the PLURONIC® series from BASF Corporation. Specifically, the PLURONIC® surfactants which are especially suited for use are identified as PLURONIC® P103, P104, and P105. Among these, PLURONIC® P103 is most preferred. PLURONIC® P103, P104, and P105 have a hydrophobe base molecular weight of about 3250, and an ethylene oxide content of 30 percent, 40 percent and 50 percent by weight, respectively. These PLURONIC® polyols are in paste form and serve to bring the organo-phosphorous insecticide into emulsion with the water to form an all aqueous emulsion of the organo-phosphorous pesticides.

The compositions also include the use of urea. The use of the urea functions to ameliorate the malodor problem inherent in organo phosphorous compositions and especially inherent in those formulations which utilize phosphorothioates. Urea also functions as a phase stabilizer for the composition so that the urea, in combination with the surfactant, serves to bring the organo-phosphorous active agent into a sprayable liquid emulsion form. Those skilled in the art will recognize that many other phase stabilizers can be substituted for urea and that all such phase stabilizers are included within the invention. The urea is present in an amount sufficient to phase stabilize the composition, and preferably is present in an amount of from about 3 to 16 percent by weight of the composition. Urea also aids in thickening the composition by competing with the surfactant for the water in the formulations.

The balance of composition also includes water, preferably from about 20 to 50 percent by weight of the composition. The composition is solvent free and completely water based. Thus, it is safe for use around automobile finishes such as would be encountered during spraying operations in residential areas. The composition is also suited for use in agriculture and does not contain any organic solvents which are toxic to fish and wild life. Accordingly, the toxicity of the byproducts of the formulations due to run-off of the formulations into streams and water tables is greatly reduced.

The formulations are ideally made in the following manner. The surfactant is added to water under moderate agitation. The agitation should be adjusted such that minimal foam is generated during the addition of the surfactant. Urea is added to the surfactant water solution and the pesticide is added under agitation. The use of urea is preferred to give enhanced phase stabilization. However, various other phase stabilizers as occur in the art may be utilized in this invention. The preferred formulation contains an organo-phosphorous pesticide, and particularly a pesticide agent in an amount of about 65 percent by weight of the composition, urea, in an amount of about 8 percent by weight of the composition, a surfactant, in an amount of about 7 percent by weight of the composition, and water, in an amount of about 20 percent by weight of the composition.

The formulations of the present invention may be used as is or diluted with water and used as a dip or spray for both plants and animals, as well as for human beings.

The following examples are offered to illustrate various aspects of the invention. Those skilled in the art will understand that they are not to be construed in any way as limiting the scope and spirit of the invention. All weights are given in weight percent of the composition.

TABLE I

| Example | 1 | 2 | 3 | 4 | 5 | 6 | 7 | 8 |
|---|---|---|---|---|---|---|---|---|
| Malathion | 95.0 | 80.0 | 80.0 | 90.0 | 70.0 | 40.0 | 40.0 | 65.0 |
| PLURONIC ® P103 | 5.0 | 5.0 | 3.0 | 1.0 | 3.0 | 1.0 | 3.0 | 7.0 |
| Water | — | 15.0 | 5.0 | 6.0 | 12.0 | 53.0 | 51.0 | 20.0 |
| Urea | — | — | 12.0 | 3.0 | 15.0 | 6.0 | 6.0 | 8.0 |
| | 100.0 | 100.0 | 100.0 | 100.0 | 100.0 | 100.0 | 100.0 | 100.0 |

Example 1 illustrates that PLURONIC ® P103 will dissolve in straight malathion, without the need for water or any organic solvents. The mixture was a clear solution, indicating that no emulsion was formed. The viscosity of the formulation was measured with a Brookfield #2 spindle. The Brookfield Viscosity was 350 mPa at 6 rpm, and 85 mPa at 60 rpm. The viscosity parameters indicate that the presence of the surfactant served to thicken the formulation, which suggests that the surfactant can contribute to storage stability, and when subjected to agitation, the formula sheared thin, thereby facilitating spraying operations.

Example 2 illustrates the formulation of malathion and PLURONIC ® P103 in water, as an emulsion. The example illustrates that no organic solvents are necessary, as in the prior art, to form a usable emulsion of Malathion and water. The emulsion formed was a white, opaque emulsion. The viscosity, as measured with a Brookfield #2 spindle was 500 mPa at 6 rpm and 145 mPa at 60 rpm. The emulsion was phase stable for only a short period of time, i.e., several days. This illustrates that although a usable emulsion was possible without urea, it was not sufficiently phase stable to withstand extended storage periods without the need to re-mix the formula to produce the aqueous emulsion.

Example 3 illustrates a phase stable emulsion of malathion, PLURONIC ® P103, urea and water. The formulation was phase stable for at least several weeks due to the presence of urea. Urea is demonstrated here as a phase stabilizer. Urea may also be termed as a thickener, but any thickening due to urea was probably due to competition between urea and PLURONIC ® for water to solubilize with. The emulsion formed was a white colored fluid and the viscosity, as measured with a Brookfield #2 spindle was 500 mPa at 6 rpm and 90 mPa at 60 rpm. By comparing this with the viscosity of Example 2, one can see that the amount of surfactant present is most determinative of the viscosity.

Example 4 illustrates a formulation which was outside the ranges of the present invention. The emulsion formed was light tan in color with some solids present in the formulation. The solids were presumably urea. Because of the small amount of water present, the urea and PLURONIC ® P103 competed for the available water. The emulsion was not phase stable. The viscosity, as measured on a Brookfield #2 spindle was 950 mPa at 6 rpm and 180 mPa at 60 rpm.

Example 5 illustrates another formulation outside the ranges of the present invention because it did not form a free flowing, sprayable, readily dilutable liquid. In this case, the large amount of urea was able to compete with the PLURONIC ® P103 for the available water. The result was initially a solid gel cake. This illustrates that urea also has some thickening properties in addition to its phase stabilizing properties. No viscosity measurements were initially taken.

Example 6 illustrates an aqueous phase stable emulsion of Malathion, PLURONIC ® P103, water and urea. The emulsion formed was white colored and the viscosity, as measured with a Brookfield #2 spindle, was 150 mPa at 6 rpm and 40 mPa at 60 rpm. The formulation was initially phase stable, for at least several weeks, but, because of the thin nature of the emulsion, was not expected to show stability over an extended shelf life.

Example 7 illustrates another aqueous, emulsion of malathion, PLURONIC ® P103, water and urea. The emulsion formed was white, and the Brookfield viscosity with a #2 spindle was 900 mPa at 6 rpm and 95 mPa at 60 rpm. This formula was not phase stable because of the high water content, and illustrated that the range of PLURONIC ® P103 is critical to viscosity of the formula. The formula was initially phase stable, but did not exhibit phase stability over an extended period.

Example 8 shows the optimum formulation for the emulsions of the present invention. The emulsion was white, and phase stable over an extended period. Thus, shelf life was expected over any storage period. The viscosity as measured on a Brookfield #3 spindle was 4800 at 6 rpm and 1200 at 60 rpm. Measurements using the Brookfield #2 spindle were off the scale.

The following example illustrates a comparison of the relative phase stability and viscosity of emulsions of Malathion, using different components as surfactants. The emulsions had the following composition:

| | Example 9 |
|---|---|
| Malathion | 65.0% |
| Urea | 8.0% |
| Surfactant* | 6.5% |
| Water | 20.5% |
| | 100.0% |

*The surfactants compared in the formulation were selected from the following list of nonionic surfactants. The surfactants were compared by using each separately in the formulation of Example 9.

*Surfactants compared
  Nonylphenol-9 mole ethoxylate, (A)
  Nonylphenol-40 mole ethoxylate, (B)
  Castor Oil-36 mole ethoxylate, (C)
  PLURONIC ® P103, (D)

The relative viscosities, as measured with a Brookfield #2 spindle at 20° C., of the formulations containing (A) or (B) were 125 mPa at 6 rpm and 95 mPa at 60 rpm for a formulation using (A) as a surfactant, and 150 mPa at 6 rpm and 128 mPa at 60 rpm for a formulation using (B) as a surfactant. There was no long lasting phase stability in either formulation and without agitation, the formulas would not form emulsions. Neither formulation containing (A) or (B) was phase stable for more than 24 hours.

An analogous formulation containing (C) as a surfactant was made. The viscosity, as measured with a Brookfield #2 spindle at 20° C., was 700 mPa at 6 rpm and 295 mPa at 60 rpm. It can be seen that this is somewhat more viscous than formulations utilizing surfactant (A) or (B). However, the formula with (C) as a surfactant was not phase stable for more than 24 hours. Thus, it was noted that formulations of the composition of the present invention containing (A), (B) or (C) as the surfactant did not exhibit phase stability over an extended period of time.

The analogous formulation containing (D) produced an emulsion which was phase stable for an extended period of time. The formula was observed over several weeks and no phase separation was noted. The viscosity was markedly higher than that noted for the formulations using (A), (B) or (C) as the surfactant. The viscosity for the formulation using the surfactant (D) as measured by a Brookfield #3 spindle at 20° C. was 5900 mPa at 6 rpm and 1740 mPa at 60 rpm. Measurements with the Brookfield #2 spindle were off the scale. The emulsion containing surfactant (D) was phase stable for extended periods of time, lasting several weeks, which was the observation period. The formulation also formed stable emulsions when diluted in water at any level.

EXAMPLES 10–12

Example 10 illustrates a comparison of different PLURONIC® surfactants in various Ethion formulations. Table II shows the formulations. The formulas compared "bloom" which is an indication of the miscibility of one liquid within another, as well as an indication of viscosity.

TABLE II

| Example | 10 | 11 | 12 |
| --- | --- | --- | --- |
| Ethion | 65.0 | 65.0 | 65.0 |
| Water | 20.0 | 20.0 | 20.0 |
| Urea | 8.0 | 8.0 | 8.0 |
| PLURONIC ® P103 | — | 7.0 | — |
| PLURONIC ® P104 | 7.0 | — | — |
| PLURONIC ® P105 | — | — | 7.0 |
|  | 100.0 | 100.0 | 100.0 |

The formulation of Example 10 demonstrated good bloom when diluted 100 times in water. The bloom patterns illustrate that it was not very viscous. The formulation was initially phase stable, but after about two months, syneresis was observed and a clear layer was observed. Thus, the phase stability was questionable after two months.

The formulation of Example 11 demonstrated diminished bloom as compared to Example 10 when diluted 100 times in water. This formulation demonstrated greater viscosity than Example 10. The formula exhibited excellent phase stability at any dilution, with no phase separation after two months.

The formulation of Example 12 exhibited a bloom similar to the formulation of Example 10. Thus, it can be assumed that it was relatively thin. The formula was initially phase stable, but after two months, a syneresis was observed and phase separation occurred. The formula was diluted 100 times in water, and after two months, phase separation occurred.

The embodiments of the invention in which an exclusive property or privilege is claimed are defined as follows:

1. An aqueous, phase stable, homogenous emulsion composition of phosphorothioate pesticides which is free of organic solvents, comprising:
   (a) a phosphorothioate pesticide present in an amount from about 40 to 95 percent by weight of the composition;
   (b) a nonionic block, heteric, or heteric/block copolymer surfactant present in an amount of about 3 to 10 percent by weight of the composition, said surfactant having the formula $HO(C_2H_4O)_m(C_3H_6O)_n(C_2H_4O)_mH$ wherein n has a value such that the molecular weight of the hydroprobe $(C_3H_6O)$ is about 3250, and m has a value such that the oxyethylene chains constitute about 30 to 50 weight percent of the surfactant;
   (c) urea, present in an amount of about 3 to 16 percent by weight of the composition; and,
   (d) water, present in an amount of about 20 to 50 percent by weight of the composition.

2. The composition of claim 1, wherein the phosphoronthioate pesticide is selected from the group consisting of O-diethyl S-(p-chlorophenylthio)methyl phosphorodithioate, O,O-dimethyl phosphorodithioate of dimethylmercapto succinate, N-(mercaptomethyl)-phthalimido S-(O,O-dimethyl) phosphorodithioate, O,O,O'O-tetraethyl S,S'-methylenediphosphorodithioate, and mixtures thereof.

3. A method for producing an aqueous, phase stable, homogenous emulsion composition of phosphorothioate pesticides which is free of organic solvents comprising blending together under moderate agitation an emulsifying amount of a nonionic block, heteric or heteric/block copolymer surfactant present in an amount of about 3 to 10 percent by weight of the composition, said surfactant having the formula $HO(C_2H_4O)_m(C_3H_6O)_n(C_2H_4O)_mH$ wherein n has a value such that the molecular weight of the hydroprobe $(C_3H_6O)$ is about 3250, and m has a value such that the oxyethylene chains constitute about 30 to 50 weight percent of the surfactant; a pesticidally effective amount of a phosophorothioate pesticide which is present in an amount from about 40 to 95 percent by weight of the composition; a phase stabilizing amount of urea, present in an amount of about 3 to 16 percent by weight of the composition; and water, present in an amount of about 20 to 50 percent by weight of the composition.

4. The method of claim 3 wherein the phosphorothioate pesticide is selected from the group consisting of O,O-diethyl S-(p-chlorophenylthio)methyl prosphorodithioate, O,O-dimethyl phosphorodithioate of dimethylmercapto succinate, N-(mercaptomethyl)-phthalimido S-(O,O-dimethyl)phosphorodithioate, O,O,O'O-tetraethyl S,S'-methylene-diphosphorodithioate, and mixtures thereof.

* * * * *